(12) United States Patent
Kruijsen et al.

(10) Patent No.: US 8,353,807 B2
(45) Date of Patent: Jan. 15, 2013

(54) DROP FOOT DEVICE

(75) Inventors: Lambertus Joseph Martinus Kruijsen, Uden (NL); Günter Gneiting, Nürtingen (DE)

(73) Assignee: Ossur Europe B.V., Son (NL)

( * ) Notice: Subject to any disclaimer, the term of this patent is extended or adjusted under 35 U.S.C. 154(b) by 0 days.

(21) Appl. No.: 13/407,946

(22) Filed: Feb. 29, 2012

(65) Prior Publication Data

US 2012/0157903 A1 Jun. 21, 2012

Related U.S. Application Data

(63) Continuation of application No. 12/986,345, filed on Jan. 7, 2011, now Pat. No. 8,137,246, which is a continuation of application No. 12/577,808, filed on Oct. 13, 2009, now Pat. No. 7,918,765, which is a continuation of application No. 10/980,975, filed on Nov. 3, 2004, now Pat. No. 7,674,212, which is a continuation of application No. PCT/NL02/00298, filed on May 6, 2002, now Pat. No. 7,674,212.

(51) Int. Cl.
*A63B 21/00* (2006.01)

(52) U.S. Cl. .......................... 482/79; 482/80

(58) Field of Classification Search .......... 482/124, 482/105, 79, 126, 80
See application file for complete search history.

(56) References Cited

U.S. PATENT DOCUMENTS

| | | |
|---|---|---|
| 2,477,591 A | 8/1949 | Follis |
| 2,663,294 A | 12/1953 | Harrison |
| 2,717,387 A | 9/1955 | McMahan |
| 2,733,443 A | 2/1956 | Holder |
| 3,527,209 A | 9/1970 | Baker |
| 4,273,328 A | 6/1981 | Ozbey et al. |
| 4,329,982 A | 5/1982 | Heaney |
| 4,559,934 A | 12/1985 | Philipp |
| 4,651,723 A | 3/1987 | Satoh |
| 4,829,982 A | 5/1989 | Abidor |
| 5,088,480 A | 2/1992 | Wang |
| 5,135,217 A | 8/1992 | Swain |
| 5,297,294 A | 3/1994 | Washick |

(Continued)

FOREIGN PATENT DOCUMENTS

| | | |
|---|---|---|
| DE | 327 817 C | 10/1920 |
| DE | 19 70 630 U | 10/1967 |
| FR | 2 586 907 A | 3/1987 |
| WO | 0135876 A | 5/2001 |

OTHER PUBLICATIONS

International Search Report issued in related PCT/NL02/00298, Jan. 21, 2003, 3 pages.

*Primary Examiner* — Jerome W Donnelly

(74) *Attorney, Agent, or Firm* — Bacon & Thomas, PLLC

(57) ABSTRACT

A method for compensating functional disabilities of the foot of a wearer including the steps of placing a shoe on a wearer; attaching a first attachment member about a lower leg of the wearer such that the first attachment member has a first connecting member flexibly extending from the first attachment member and directed toward the foot; attaching a second attachment member in engagement with a shoe placed over the wearer's foot such that the second attachment has a second attachment member flexibly extending therefrom and directed toward the lower leg of the wearer. The first and second connecting members are coupled such that the flexible connecting member extends at an acute angle from the lower leg of the wearer at a point above the joint of a leg and foot to a point forward of the leg at the instep of the foot.

17 Claims, 1 Drawing Sheet

U.S. PATENT DOCUMENTS

| | | |
|---|---|---|
| 5,813,955 A | 9/1998 | Gutkowski et al. |
| 5,898,939 A | 5/1999 | Schramm |
| 6,178,555 B1 | 1/2001 | Williams |
| 6,602,217 B2 | 8/2003 | Crawford et al. |
| 6,955,616 B1 | 10/2005 | Barth et al. |
| 7,153,246 B2 | 12/2006 | Koscielny et al. |
| 7,179,206 B2 | 2/2007 | Backes et al. |
| 2003/0040408 A1 | 2/2003 | Cooper, Sr. |

DROP FOOT DEVICE

CROSS-REFERENCE TO RELATED APPLICATIONS

This application is a continuation of U.S. patent application Ser. No. 12/986,345, filed Jan. 7, 2011, which is a continuation of U.S. patent application Ser. No. 12/577,808, filed Oct. 13, 2009, which is a continuation of U.S. patent application Ser. No. 10/980,975, filed Nov. 3, 2004, which is a continuation of PCT International Application No. PCT/NL02/00298 filed May 6, 2002, the contents of which are hereby incorporated by reference in their entirety.

BACKGROUND OF THE INVENTION

1. Field of the Invention

This invention relates to an assembly of an accessory and a shoe for supporting a foot-drop affected foot relative to a lower leg belonging to the foot such that the foot is prevented from dropping down relative to the lower leg when the foot is raised by the lower leg from a supporting surface, the accessory being provided with a first attachment member for attachment of the accessory to the lower leg, a second attachment member for attachment of the accessory to an upper side of the shoe, and a connecting body joining together the first attachment member and the second attachment member. Further, the invention relates to an accessory of the assembly for providing (bottom) support to a foot-drop affected foot.

2. Prior Art

The referred-to assembly is known and is described in, for instance, U.S. Pat. No. 4,829,982. In the known assembly, the shoe of the assembly is provided with a special modification for attaching the second attachment member to the shoe.

A disadvantage of the known assembly is that the shoe of the assembly is restricted to a particular type. The shoe of the known assembly is provided with a clearly visible attaching eye. One of the consequences thereof is that the user is not free to choose the type of shoe to be used. Attaching the accessory to the shoe with the first attachment member takes place in a conspicuous and laborious manner. Besides, it holds that the point of engagement of the second attachment member is not at mid-length of the shoe, so that a twisting supporting force is applied to the shoe with the foot-drop affected foot.

SUMMARY OF THE INVENTION

It is an object of the present invention to meet at least one of the above-mentioned disadvantages. To that end, the invention provides an assembly which is characterized in that the second attachment member is provided with an attachment plate which, in use, is positioned under an upper part of the shoe. Thus, a relatively inconspicuous attachment can be realized. Further, with this attachment, it is possible to use a large number of different types of shoes in the assembly, so that the user has a large freedom of choice in determining the type of shoe desired by him/her. In particular, the user can opt for a relatively inconspicuous "normal" shoe.

According to a preferred embodiment of the assembly it holds that with the attachment plate, the accessory can be detachably connected to the shoe. If the shoe is a lace-up shoe, the attachment plate can be positioned between at least a part of the lace and an upper tongue extending in the longitudinal direction of the shoe while, in use, the attachment plate is laced between the lace and the upper tongue. However, with a lace-up shoe, it is also possible that the attachment plate is positioned in at least a part of the lace and, during use, is laced in the lace. Thus, by means of the attachment plate, the accessory can be detachably connected in a simple manner with virtually any type of lace-up shoe. The attachment plate can be arranged at a position such that the resultant of the supporting force to be transmitted acts on the shoe at a desired location. Consequently, it is possible, inter alia, viewed in a transverse direction of the shoe, to have the resultant act at mid-length of the shoe, so that in the transverse direction, the foot-drop affected foot does not experience, or hardly experiences torsion of the supporting force.

According to one embodiment, it holds that the attachment plate is manufactured from a flexible material. As a result, the plate can be modeled on, for instance, the instep of the foot-drop affected foot for obtaining a favorable comfort in wearing. Preferably, it holds that the connecting plate attachment strap is provided with a Velcro closure for opening and closing the strap, so that the strap can be rapidly and fittingly attached to the leg.

According to a preferred embodiment it holds that the connecting body is substantially provided with a strip-shaped part. The strip-shaped part can be designed to be flexible for obtaining an optimal supporting characteristic. According to this supporting characteristic, the upward force applied to the foot-drop affected foot can be adapted to the relative position of the foot-drop affected foot relative to the leg in a dynamic manner which is well in line with the natural way of walking. Preferably, the strip-shaped part is provided with a first strip-shaped subpart and a second strip-shaped subpart and a closure for detachably joining together the first and the second strip-shaped subpart. As a result, the attachment strap can be disconnected from the shoe in a simple manner. When the user, while sitting down, has no need for (bottom) support or wishes to take his shoe off, the accessory can be disconnected from the shoe without the attachment plate having to be detached from the shoe.

The invention also relates to the accessory of the assembly as further defined in the appended claims.

BRIEF DESCRIPTION OF THE DRAWINGS

The invention will presently be further elucidated with reference to the drawings. In the drawings.

DETAILED DESCRIPTION OF PREFERRED EMBODIMENTS OF THE INVENTION

Figure 1:
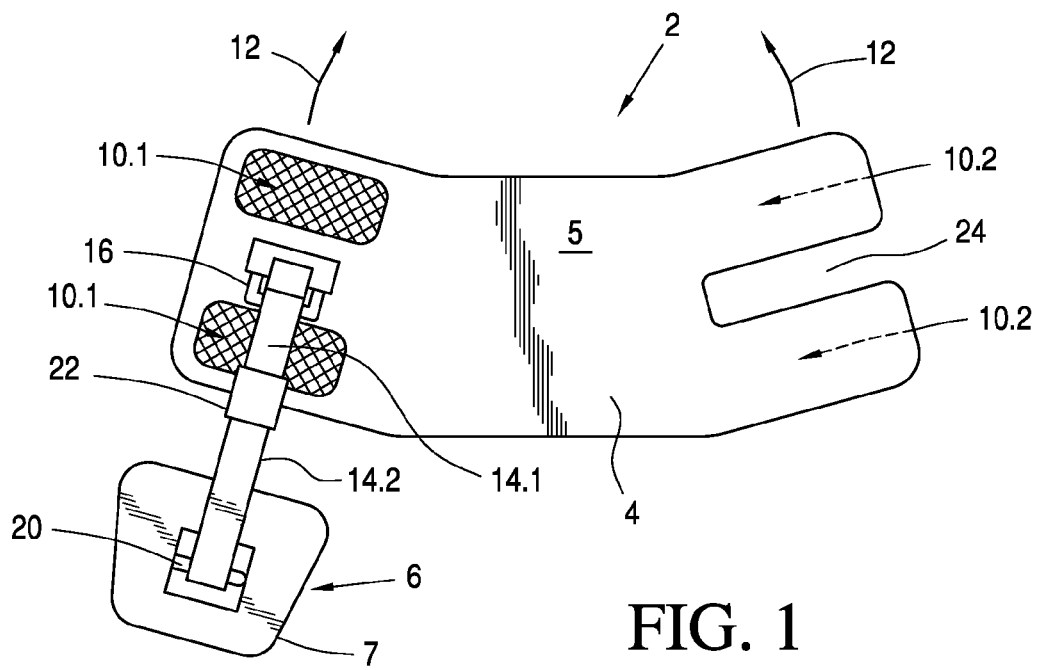
FIG. 1 is a schematic perspective representation of the accessory according to the invention.

In FIG. 1, an accessory 2 is shown for supporting a foot-drop affected foot relative to a lower leg belonging to the foot such that the foot is prevented from dropping down relative to the lower leg when the foot is raised by the lower leg from a supporting surface. The accessory is provided with a first attachment member 4 for attachment of the accessory 2 to the lower leg, a second attachment member 6 for attachment of the accessory 2 to an upper side of a shoe 8 enclosing the foot-drop affected foot, and a connecting body 14 joining together the first attachment member 4 and the second attachment member 6. The second attachment member 6 is provided with an attachment plate 7 which, in use, is positioned under an upper part (such as a tongue, shoe lace or edge) of the shoe 8 (see FIG. 2).

In this example, the first attachment member 4 is an attachment strap 5, provided with first Velcro parts 10.1 which can cooperate with second Velcro parts 10.2 for closing the strap 5. Thus, the strap 5 can be attached around the leg relatively rapidly in a fitting manner. With the arrows 12 in FIG. 1, it is indicated in which manner the strap for the above-mentioned attachment can be wrapped around the leg with the foot-drop affected foot.

In this example, the connecting body 14 is substantially provided with a strip-shaped part connected by a hinged joint connection 16 to the strap 5 and connected by a hinged joint connection 20 to the attachment plate 7. The strip-shaped part is preferably manufactured from a flexible material with which a favorable supporting characteristic of the foot-drop affected foot is obtained. Using hinged joint connections 16, 20 is advantageous because movements of the foot-drop affected foot relative to the leg can be followed well, yet the hinged joint connections are not a requisite in any manner for achieving the object of the invention. The strap 5 is provided with a recess 24 in which the point of attachment of the strap 5 and the connecting body 14 can be received when wrapping the strap 5 around the leg with the foot-drop affected foot.

The strip-shaped part of the connecting body 14 is provided with a quick-acting closure 22 for detachably joining together a first strip-shaped subpart 14.1 and a second strip-shaped subpart 14.2. With the quick-acting closure 22, the strap 5 can be disconnected from the connecting plate 7.

Figure 2:
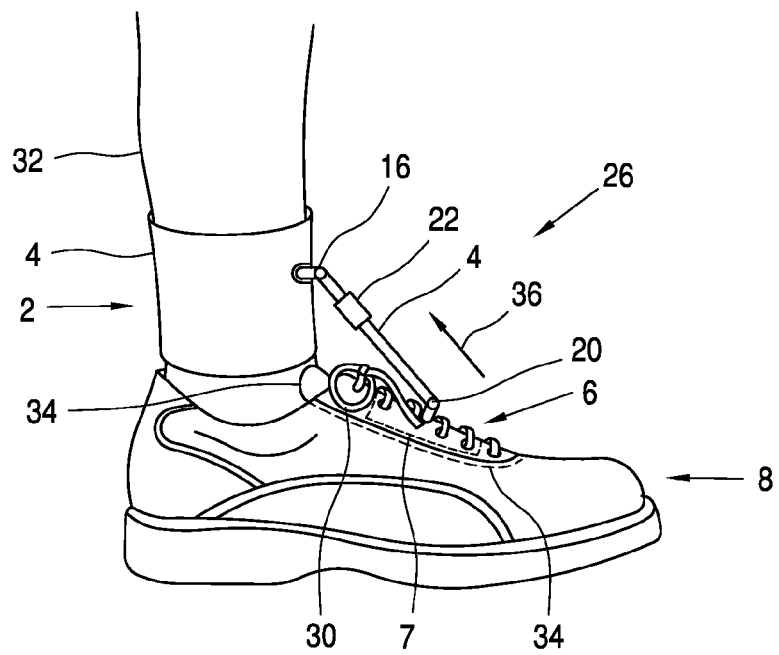
FIG. 2 is a schematic perspective side view of an assembly according to the invention which is put into use by a person having a foot-drop affected foot.

In FIG. 2 an assembly 26 of an accessory 2 and a shoe 8 for providing 30 (bottom) support to the foot-drop affected foot is shown. The shoe according to the example of FIG. 2 is a lace-up shoe with a lace 30. For attachment of the accessory, the strap 5 has been wrapped around a lower leg 32 of a user. Further, the connecting plate 7 mentioned is attached to the shoe 8. This attachment can take place in various manners. According to a first possible manner of attachment, the attachment plate 7 is positioned between at least a part of the lace 30 and an upper tongue 34 extending in the longitudinal direction of the shoe so that, during use, the plate 7 is forced between the lace 30 and the upper tongue 34. In this case, the plate 7 lies completely under the lace 30. According to a second manner of attachment, the plate 7 is positioned in at least a part of the lace 30 and is laced, in use, in the lace 30. Here, the plate lies between overlying parts of the lace 30 and underlying parts of the lace 30. With both possibilities, viewed in the longitudinal direction of the shoe, the attachment plate 7 can at least partly be enclosed by a part of the lace 30. Optionally, the attachment plate 7 is provided with lacing eyelets for pulling through the lace 30.

In FIG. 2, the connecting plate 7 and the tongue 34 are schematically represented in dotted lines. Here, the second attachment possibility mentioned is shown. After closure of the shoe by tightening the lace 30, the connecting plate 7 is clamped in between the tongue 34 and the lace 30 and, optionally the tightened edges of the shoe 8. If the first part of the connecting body 14.1 is joined to the second part of the connecting body 14.2 by means of the closure 22, then the user, when walking, experiences an upward (supporting) force 36 which acts on a point located near the tongue 34 of the shoe 8.

Attaching the accessory to the shoe by means of the connecting plate 7 enables use of the accessory in combination with virtually any type of shoe and in particular with virtually all lace-up shoes. Therefore, the user is not hindered in the choice of shoes desired by him. Preferably, the attachment plate 7 is manufactured from a flexible material which can model itself on the shape of the instep of the shoe and the foot-drop affected foot enclosed by the shoe. Further, it holds that, preferably, the attachment plate tapers slightly in a direction away from the connecting body 14. With these features, a good adaptation of the attachment member 6 to the shoe 8 is obtained, thereby realizing favorable comfort in wearing.

The supporting force 36 is determined by the type of material of the connecting body and the length of this strip. Optionally, the connecting body 14 can be provided with several closing elements 22, so that different connecting subbodies of, for instance, different materials and different lengths can be fitted into the accessory for obtaining the supporting characteristic of the upwardly directed (supporting) force 36 desired by the user. The upwardly directed (supporting) force 36 is transmitted via the shoe 8 to the foot-drop affected foot. When, at any time, the user does not need the (supporting) force 36, the user can undo the closure 22. It is also possible, after undoing the closure 22, to take the shoe 8 off without the attachment plate 7 having to be detached from the shoe 8.

During use of the assembly according to the invention an effective couple is applied to the shoe 8 via the upward force 36, inter alia because the point of engagement of the force 36 to the shoe 8 is located at a distance from the hinge point of the foot-drop affected foot. Thus, with a relatively limited force 36, a considerable couple for supporting the foot-drop affected foot is given. As no great forces need to act on the assembly, it can have a relatively long life span.

By designing the connecting plate 7 to be transparent, the accessory is hardly visible. Further, the strap 7 and/or the connecting body 14 can be provided with an appropriate color such as, for instance, black, so as to realize an inconspicuous accessory 2. The assembly and the accessory according to the invention have been described on the basis of one embodiment. However, the assembly and the accessory are not limited in any way to the described embodiment. Various variations are possible which are also understood to fall within the framework of the invention.

The invention claimed is:

1. A method for compensating functional disabilities of a foot of a wearer, comprising:
    attaching a first attachment member about a lower leg of the wearer, the first attachment member having a first connecting member flexibly extending from the first attachment member and directed toward the foot;
    placing a second attachment member formed from a flexible material over the wearer's foot and adapting to the shape of the foot, the second attachment member located in the area of the instep of the foot, the second attachment having a second connecting member extending therefrom and directed toward the lower leg of the wearer;
    coupling the first and second connecting members, such that at least the first connecting member extends at an acute angle from the lower leg of the wearer at a point above a joint of the leg and foot to a point forward of the leg at the instep of the foot;
    wherein at least one of the first and second connecting members is elastic.

2. A method for compensating functional disabilities of a foot of a wearer, comprising:
    attaching a first attachment member about a lower leg of the wearer, the first attachment member having a first connecting member flexibly extending from the first attachment member and directed toward the foot;
    placing a second attachment member formed from a flexible material over the wearer's foot and adapting to the shape of the foot, the second attachment member located in the area of the instep of the foot, the second attachment having a second connecting member extending therefrom and directed toward the lower leg of the wearer;

coupling the first and second connecting members, such that at least the first connecting member extends at an acute angle from the lower leg of the wearer at a point above a joint of the leg and foot to a point forward of the leg at the instep of the foot;

wherein first and second coupling elements are located at end portions of the first and second connecting members, respectively.

3. A method for compensating functional disabilities of a foot of a wearer, comprising:

attaching a first attachment member about a lower leg of the wearer, the first attachment member having a first connecting member flexibly extending from the first attachment member and directed toward the foot;

placing a second attachment member formed from a flexible material over the wearer's foot and adapting to the shape of the foot, the second attachment member located in the area of the instep of the foot, the second attachment having a second connecting member extending therefrom and directed toward the lower leg of the wearer;

coupling the first and second connecting members, such that at least the first connecting member extends at an acute angle from the lower leg of the wearer at a point above a joint of the leg and foot to a point forward of the leg at the instep of the foot;

further comprising the step of adjusting the length of at least one of the first and second connecting members.

4. The method according to claim 2, further comprising the step of adjusting the length of at least one of the first and second connecting members via at least one of the first and second coupling elements.

5. The method according to claim 1, further comprising the step of:

placing a shoe on a wearer, the shoe having a toe portion, a heel portion and an instep portion, the instep portion having on its upper side an upper closure that when open enables a foot to be inserted into the shoe and when closed for maintaining the shoe on the foot;

attaching the second attachment member in engagement with the shoe placed over the wearer's foot.

6. The method according to claim 5, further comprising the step of clamping the second attachment member against the instep portion of the shoe via securing shoe upper parts against the foot of the wearer.

7. The method according to claim 5, wherein the second attachment member is adjustable relative to the instep area of the shoe and is securable underneath a plurality of laces belonging to the shoe and only at a region corresponding to the plurality of laces.

8. A method for compensating functional disabilities of a foot of a wearer, comprising:

attaching a first attachment member about a lower leg of the wearer, the first attachment member having a first connecting member flexibly extending from the first attachment member and directed toward the foot;

placing a second attachment member formed from a flexible material over the wearer's foot and adapting to the shape of the foot, the second attachment member located in the area of the instep of the foot, the second attachment having a second connecting member extending therefrom and directed toward the lower leg of the wearer;

coupling the first and second connecting members, such that at least the first connecting member extends at an acute angle from the lower leg of the wearer at a point above a joint of the leg and foot to a point forward of the leg at the instep of the foot;

wherein the second attachment member includes an attachment plate formed from a flexible material and arranged to be placed over only a top portion at an instep area of the wearer's foot.

9. The method according to claim 2, wherein the first and second coupling elements have a plurality of locations longitudinally spaced along the elongated flexible connecting member for selectively and detachably holding together the two coupling elements longitudinally aligned.

10. The method according to claim 9, wherein the attachment plate tapers in width in a direction of the toe portion of the foot.

11. A method for compensating functional disabilities of the foot of a wearer, comprising:

attaching a first attachment member about a lower leg of the wearer, the first attachment member having a first connecting member flexibly extending from the first attachment member and directed toward the foot;

attaching a second attachment member in engagement with a shoe placed over the wearer's foot, the second attachment having a second attachment member flexibly extending therefrom and directed toward the lower leg of the wearer;

coupling the first and second connecting members such that the flexible connecting member extends at an acute angle from the lower leg of the wearer at a point above the joint of a leg and foot to a point forward of the leg at an instep portion of the foot;

wherein at least one of the first and second connecting members is elastic.

12. The method according to claim 11, wherein the second attachment member is placed in engagement with the shoe in the area of the instep of the foot.

13. The method according to claim 11, wherein the first and second connecting members are connected via first and second mutually coacting coupling elements, respectively, mounted on end portions of the first and second connecting members.

14. The method according to claim 13, wherein the mutually coacting coupling elements provide a plurality of locations longitudinally spaced along the elongated flexible connecting member for selectively and detachably holding together the two elements longitudinally aligned.

15. The method according to claim 13, further comprising the step of adjusting the length of the first connecting member via the first mutually coacting coupling element.

16. The method according to claim 13, further comprising the step of adjusting the length of the second connecting member via the second mutually coacting coupling element.

17. A method for compensating functional disabilities of a foot of a wearer, comprising:

attaching a first attachment member about a lower leg of the wearer, the first attachment member having a first connecting member flexibly extending from the first attachment member and directed toward the foot;

securing a second attachment member to a wearer's foot, the second attachment having a second attachment member flexibly extending therefrom and directed toward the lower leg of the wearer;

coupling the first and second connecting members such that the flexible connecting member extends at an acute angle from the lower leg of the wearer at a point above the joint of a leg and foot to a point forward of the leg at an instep portion of the foot;
wherein the first and second connecting members are connected via first and second mutually coacting coupling elements, respectively, mounted on end portions of the first and second connecting members;
wherein the second attachment member includes an attachment plate formed from a flexible material and arranged to be placed over only a top portion at an instep area of a wearer's foot.

* * * * *